US00PP21768P2

(12) United States Plant Patent
Kawashima

(10) Patent No.: US PP21,768 P2
(45) Date of Patent: Mar. 8, 2011

(54) **NEW GUINEA *IMPATIENS* PLANT NAMED 'SAKIMP018'**

(50) Latin Name: *Impatiens×hybrida*
Varietal Denomination: SAKIMP018

(75) Inventor: Moriya Kawashima, Amstelveen (NL)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/586,961

(22) Filed: Sep. 30, 2009

(51) Int. Cl.
*A01H 5/00* (2006.01)

(52) U.S. Cl. ..... Plt./318.2

(58) Field of Classification Search ..... Plt./318.2
See application file for complete search history.

*Primary Examiner*—Susan B McCormick Ewoldt
(74) *Attorney, Agent, or Firm*—Jondle & Associates, P.C.

(57) ABSTRACT

A New Guinea *Impatiens* plant particularly distinguished by having white flowers, variegated leaves, a short, outwardly growing, trailing, and loose plant frame, and strong root system is disclosed.

1 Drawing Sheet

Genus and species: *Impatiens×hybrida.*
Variety denomination: 'SAKIMP018'.

BACKGROUND OF THE NEW PLANT

The present invention relates to a new and distinct cultivar of New Guinea *Impatiens*, botanically known as *Impatiens× hybrida*, and referred to by the variety name 'SAKIMP018'. 'SAKIMP018' originated from an interspecific hybridization between the female *Impatiens* plant 'NB-362', an unpatented proprietary *Impatiens* breeding line with a white flower color and small, tight plant frame, and the male *Impatiens* plant, 'EL-1A-2', an unpatented proprietary *Impatiens* breeding line with a lilac flower color and vigorous plant growth habit, in Misato, Japan.

In February 2005, the female parent line 'NB-362' and male parent line 'EL-1A-2' were crossed and a population of $F_1$ plants was created. The new variety was first propagated via vegetative cuttings in Salinas, Calif. and has been asexually reproduced repeatedly by vegetative cuttings. The $F_1$ plants were evaluated in Misato, Japan in an open field trial. The criteria for plant selection included a white flower color, variegated leaves, strong root system, and short, outwardly growing, trailing, and loose plant frame. At the completion of the trial, one single-plant selection was made based on the above criteria and vegetatively propagated. From May to August 2006, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP018' and found to have its unique characteristics reproduced true to type in successive generations of asexual propagation.

SUMMARY OF THE INVENTION

The following are the most outstanding and distinguishing characteristics of this new cultivar when grown under normal horticultural practices in Salinas, Calif.

1. White flowers;
2. Variegated leaves;

3. Short, outwardly growing, trailing, and loose plant frame; and
4. Strong root system.

DESCRIPTION OF THE PHOTOGRAPHS

This new *Impatiens* plant is illustrated by the accompanying photographs which show the overall plant habit including blooms, buds, and foliage of the plant; the colors shown are as true as can be reasonably obtained by conventional photographic procedures. The photographs are of plants that are 4 months from propagation by terminal cutting in Salinas, Calif., under greenhouse conditions.

DETAILED DESCRIPTION OF THE NEW CULTIVAR

Figure 1:
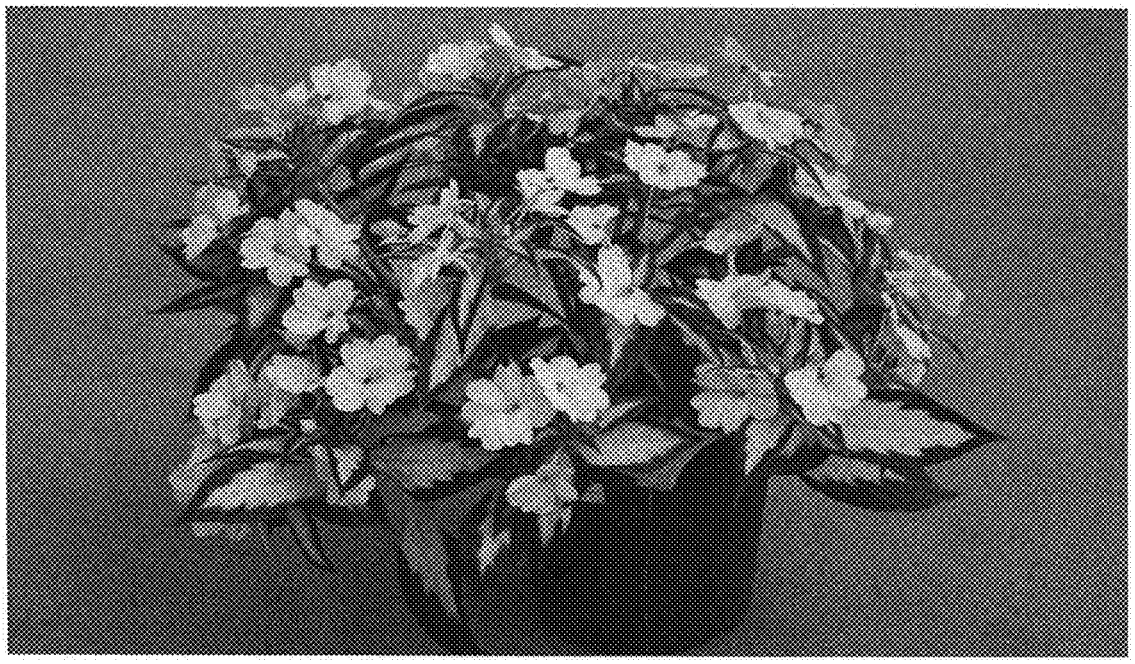
FIG. 1 shows overall plant habit including blooms, buds and foliage.
Figure 2:
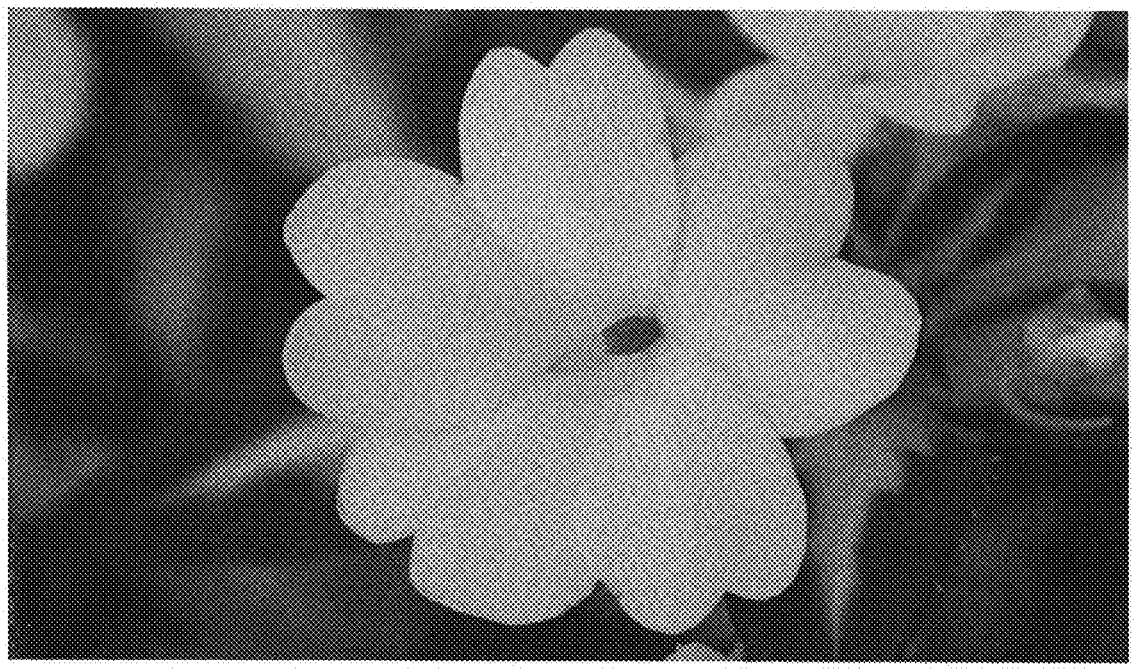
FIG. 2 shows the mature inflorescence.

The following detailed descriptions set forth the distinctive characteristics of 'SAKIMP018'. The data which define these characteristics were collected from asexual reproductions carried out in Salinas, Calif. The plant history was taken on plants grown for about 3.5 months from propagation by terminal cuttings under greenhouse conditions. Color references are primarily to The R.H.S. Colour Chart of The Royal Horticultural Society of London (R.H.S.), 4$^{th}$ edition (2001). Anatomic labels are from *The Cambridge Illustrated Glossary of Botanical Terms*, by M. Hickey and C. King, Cambridge University Press.

DETAILED BOTANICAL DESCRIPTION

Classification:
*Family.*—Balsaminaceae.
*Botanical.*—*Impatiens*×hybrid var. 'SAKIMP018'.
*Common name.*—*Impatiens.*

Parentage:
*Female parent.*—'NB-362', an unpatented proprietary white-flowered *Impatiens* plant.
*Male parent.*—'EL-1A-2', an unpatented proprietary lilac-flowered *Impatiens* plant.

Growth:

*Time to produce a rooted cutting.*—The terminal 1.0 to 1.5 inches of an actively growing stem was excised. The vegetative cuttings were propagated in five to six weeks. The base of each cutting was dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2-3 days, 2 times in consecutive applications and then given one clear water application. Pots were top-dressed with a dry, slow release fertilizer containing 14% nitrogen, 14% phosphorus and 14% potassium. The typical average air temperature was 24° C.

Plant description:

*Habit.*—Short, outwardly growing, trailing, and loose plant frame.

*Life cycle.*—Tender perennial.

*Height.*—23.0 cm to 24.0 cm from soil line to top of foliage.

*Spread.*—46.0 cm to 47.0 cm.

*Time to produce a rooted cutting.*—About 4 weeks.

*Time to bloom from propagation.*—6 to 8 weeks.

*Flowering requirements.*—Will flower so long as temperature is above 5° C.

*Temperature tolerance.*—Plants have been observed to continuously flower at a temperature range of 5° C. to 36° C.; plants can withstand high heat and humidity.

Branches:

*Number.*—3 main branches.

*Length.*—Approximately 1.0 cm from soil line to first node; approximately 3.0 cm from first node to second node; approximately 17.0 cm to 18.0 cm total.

*Diameter* (*main branch*).—0.7 cm to 0.8 cm.

*Color.*—RHS 187B (Greyed-Purple).

Stems:

*Length.*—9.0 cm.

*Diameter.*—0.5 cm.

*Internode length.*—5.5 cm.

*Color.*—RHS 48B (Red) with specks of RHS 145B (Yellow-Green).

*Stem description.*—Strong; circular cross-section, smooth and shiny.

*Pubescence.*—None.

*Anthocyanin color.*—Absent.

Leaves:

*Arrangement.*—Whorled with up to 5 leaves per node, opposite if only two leaves at one node.

*Length.*—8.5 cm.

*Width.*—4.5 cm.

*Shape.*—Lanceolate, curled.

*Margin.*—Ciliate.

*Apex.*—Acuminate.

*Base.*—Attenuate.

*Texture.*—Dull; waxy.

*Color.*—Upper surface: Variegated: RHS 8C (Yellow) at center, darkening to RHS 8A (Yellow) at edge of center variegation. Margin leaf color is RHS 139A (Green). Lower surface: RHS 191A (Greyed-Green) with RHS 8D (Yellow) at center.

*Fragrance.*—Absent.

*Pubescence.*—Glabrous.

*Variegation.*—Present.

*Venation.*—Pinnate.

*Venation color* (*both surfaces*).—RHS 150D (Yellow-Green).

*Petioles.*—Length: 1.0 cm. Diameter: 0.3 cm. Color: RHS 150D (Yellow-Green). Texture: Smooth, glabrous.

Flower buds:

*Shape.*—Deltoid, longitudinal cross-section.

*Length.*—1.8 cm.

*Diameter.*—1.0 cm.

*Color.*—RHS 155C (White).

*Texture.*—Glabrous.

Inflorescence:

*Blooming habit.*—Will flower as long as the temperature is above 5° C.

*Inflorescence type.*—Single flower with spur.

*Number of flowers per node.*—1 to 3 in bloom; about 4 to 6 flower buds per node.

*Number of flowers per plant.*—Approximately 70 in bloom.

*Lastingness of individual blooms on the plant.*—14 days.

*Fragrance.*—Absent.

Peduncles:

*Length.*—3.5 cm.

*Diameter.*—0.20 cm.

*Color.*—RHS 150D (Yellow-Green).

*Texture.*—Smooth, glabrous.

Corolla:

*Shape.*—Roughly circular with 5 radial petals.

*Diameter.*—Approximately 4.5 cm.

*Depth.*—0.3 cm.

Petals:

*Shape.*—Obcordate.

*Length.*—2.5 cm.

*Width.*—1.8 cm.

*Apex.*—Emarginate (cleaved).

*Base.*—Attenuate.

*Margin.*—Entire.

*Texture.*—Glabrous.

*Color.*—Upper surface: RHS N155A (White). Lower surface: RHS N155A (White). Eye zone: RHS N155A (White).

Spur:

*Shape.*—Tubular and curved downward.

*Color.*—RHS N155B (White).

*Length.*—4.5 cm.

*Diameter.*—0.1 cm.

Sepals:

*Shape.*—Lanceolate.

*Number.*—Two.

*Color.*—RHS 1D (Yellow-Green).

*Length.*—1.0 cm.

*Diameter.*—0.4 cm.

*Apex.*—Caudate.

*Base.*—Subcordate.

*Margin.*—Entire.

*Texture.*—Glabrous.

Reproductive organs:

*Stamens.*—Form: Fused; split into 4 lobes. Number: Many. Filament length: 0.5 cm. Filament color: RHS N155B (White). Anther length: 0.4 cm. Anther color: RHS N155A (White). Pollen amount: Abundant. Pollen color: RHS 155A (White). Pollen description: Powdery.

*Pistil.*—Number: 5. Stigma color: RHS 143A (Green). Style color: RHS 143A (Green). Style length: 0.5 cm.

*Ovary arrangement.*—Parietal.

*Ovary surface color.*—RHS 143A (Green).

Fruit and seed set: No seed set observed.

Disease and insect resistance: No particular resistance or susceptibility has been observed.

COMPARISON WITH PARENTAL AND COMMERCIAL CULTIVARS

'SAKIMP018' is similar to the female parent 'NB-362' and the male parent 'EL-1A-2', however, there are differences as listed in Table 1:

TABLE 1

Comparison of Characteristics between 'SAKIMP018' and parental cultivars

| Characteristic | 'SAKIMP018' | Male Parent 'EL-1A-2' | Female Parent 'NB-362' |
|---|---|---|---|
| Flower color | White | Lilac | White |
| Plant growth | Short, outwardly | Vigorous | Small, tight |

TABLE 1-continued

Comparison of Characteristics between 'SAKIMP018' and parental cultivars

| Characteristic | 'SAKIMP018' | Male Parent 'EL-1A-2' | Female Parent 'NB-362' |
|---|---|---|---|
| habit | growing, trailing, and loose plant frame | | plant frame |

'SAKIMP018' is similar to the commercial *Impatiens* variety 'SAKIMP014' (U.S. Plant Pat. No. 19,605); however, there are differences as listed in Table 2:

TABLE 2

Comparison of Characteristics between 'SAKIMP018' and 'SAKIMP014'

| Characteristic | 'SAKIMP018' | 'SAKIMP014' |
|---|---|---|
| Growth habit | Short, outwardly growing, trailing, and loose plant frame | Compact |
| Leaf color, upper surface | Variegated: RHS 8C (Yellow) at center, darkening to RHS 8A (Yellow) at edge of center variegation. Outer leaf color is RHS 139A (Green) | RHS 139A (Green) |
| Leaf color, lower surface | RHS 191A (Greyed-Green) with RHS 8D (Yellow) at center | RHS 137C (Green) |

I claim:

1. A new and distinct cultivar of New Guinea *Impatiens* plant as shown and described herein.

* * * * *